United States Patent
Levy et al.

(10) Patent No.: US 11,406,279 B2
(45) Date of Patent: Aug. 9, 2022

(54) METHOD AND APPARATUS FOR MONITORING THE PELVIC FLOOR MUSCLES

(71) Applicant: CHIARO TECHNOLOGY LIMITED, London (GB)

(72) Inventors: Ben Levy, London (GB); Jeroen Bergmann, Oxford (GB); Raunaq Bose, Croydon (GB); Kay Crotty, Harrow (GB)

(73) Assignee: Chiaro Technology Limited, London (GB)

(*) Notice: Subject to any disclaimer, the term of this patent is extended or adjusted under 35 U.S.C. 154(b) by 444 days.

(21) Appl. No.: 15/522,660

(22) PCT Filed: Oct. 28, 2015

(86) PCT No.: PCT/GB2015/053230
§ 371 (c)(1),
(2) Date: Apr. 27, 2017

(87) PCT Pub. No.: WO2016/067023
PCT Pub. Date: May 6, 2016

(65) Prior Publication Data
US 2017/0319103 A1 Nov. 9, 2017

(30) Foreign Application Priority Data
Oct. 28, 2014 (GB) ................................... 1419178

(51) Int. Cl.
*A61B 5/07* (2006.01)
*A61B 5/00* (2006.01)
*A61B 5/11* (2006.01)

(52) U.S. Cl.
CPC .............. *A61B 5/07* (2013.01); *A61B 5/1107* (2013.01); *A61B 5/1121* (2013.01);
(Continued)

(58) Field of Classification Search
CPC ....... A61B 5/07; A61B 5/4519; A61B 5/4337; A61B 5/1121; A61B 5/1107;
(Continued)

(56) References Cited

U.S. PATENT DOCUMENTS 5,483,832 A  1/1996 Pauser et al.
8,147,429 B2  4/2012 Mittal et al.
(Continued)

FOREIGN PATENT DOCUMENTS

EP  0 583 456 B1  9/1996
EP  1 034 016 B1  7/2007
(Continued)

OTHER PUBLICATIONS

International Search Report dated Feb. 8, 2016, issued in PCT Application No. PCT/GB2015/053230, filed Oct. 28, 2015.
(Continued)

*Primary Examiner* — Daniel L Cerioni
*Assistant Examiner* — Raymond P Dulman
(74) *Attorney, Agent, or Firm* — Sterne, Kessler, Goldstein & Fox P.L.L.C.

(57) ABSTRACT

A method of differentiating between a strain and a contraction of the pelvic floor muscles (PFM) of a subject includes receiving data generated by an orientation sensor provided within a vaginal probe device that is located within the vaginal canal of the subject and utilizing a processor to process data generated by the orientation sensor to determine a direction of rotation of the vaginal probe device during a measurement period. When the processor determines that the vaginal probe device has rotated in the cranial-ventral direction relative to the subject, an output is generated indicating that there has been a contraction of the PFM during the measurement period; and when the processor determines that the vaginal probe device has rotated in
(Continued)

the caudal-dorsal direction relative to the subject, an output is generated indicating that there has been a strain of the PFM during the measurement period.

20 Claims, 5 Drawing Sheets

(52) U.S. Cl.
CPC .......... *A61B 5/4337* (2013.01); *A61B 5/4519* (2013.01); *A61B 5/6861* (2013.01); *A61B 5/0002* (2013.01); *A61B 5/7203* (2013.01); *A61B 2560/0223* (2013.01)

(58) Field of Classification Search
CPC ..... A61B 5/6861; A61B 5/6847; A61B 5/227; A61B 5/1123; A63B 23/20
See application file for complete search history.

(56) References Cited

U.S. PATENT DOCUMENTS

| | | | |
|---|---|---|---|
| 8,172,723 B1 | 5/2012 | Yanev et al. | |
| 8,340,786 B2 | 12/2012 | Gross et al. | |
| 8,343,013 B1 | 1/2013 | Yanev et al. | |
| 2008/0105065 A1* | 5/2008 | Lee | A61B 5/112 73/865.4 |
| 2008/0262772 A1* | 10/2008 | Luinge | A61B 5/1114 702/94 |
| 2010/0174218 A1* | 7/2010 | Shim | A61B 5/1107 601/84 |
| 2011/0230782 A1* | 9/2011 | Bartol | A61B 5/4519 600/546 |
| 2011/0250575 A1 | 10/2011 | Kalvachev et al. | |
| 2012/0150074 A1 | 6/2012 | Yanev et al. | |
| 2013/0037975 A1 | 2/2013 | Thallner et al. | |
| 2013/0144191 A1* | 6/2013 | Egorov | A61B 5/227 600/591 |
| 2013/0158365 A1* | 6/2013 | Chey | A61B 5/227 600/301 |
| 2013/0274567 A1* | 10/2013 | Grosser | A61B 5/07 600/301 |
| 2013/0337974 A1 | 12/2013 | Yanev et al. | |
| 2013/0337976 A1 | 12/2013 | Yanev et al. | |
| 2014/0016945 A1 | 1/2014 | Pan | |
| 2014/0088471 A1* | 3/2014 | Leivseth | A61H 19/40 601/89 |
| 2016/0074276 A1* | 3/2016 | Scheuring | A61H 9/0071 600/479 |
| 2016/0346610 A1* | 12/2016 | Iglesias | H04W 4/80 |
| 2017/0007143 A1* | 1/2017 | Kimura | A61B 5/1118 |

FOREIGN PATENT DOCUMENTS

| | | |
|---|---|---|
| GB | 2492754 A | 1/2013 |
| WO | 00/09013 A1 | 2/2000 |
| WO | 2011/130218 A1 | 10/2011 |
| WO | 2012/031235 A1 | 3/2012 |
| WO | 2012/078718 A1 | 6/2012 |
| WO | 2012/079127 A1 | 6/2012 |
| WO | 2012/138232 A1 | 10/2012 |
| WO | 2013/147992 A1 | 10/2013 |
| WO | 2013/192084 A1 | 12/2013 |
| WO | 2015/106199 A1 | 7/2015 |

OTHER PUBLICATIONS

Written Opinion dated Feb. 8, 2016, issued in PCT Application No. PCT/GB2015/053230, filed Oct. 28, 2015.

* cited by examiner

METHOD AND APPARATUS FOR MONITORING THE PELVIC FLOOR MUSCLES

BACKGROUND OF THE INVENTION

1. Field of the Invention

The present invention relates to a method and apparatus for monitoring the action of the Pelvic Floor Muscles (PFM) of a female subject/user. In particular, the present inventions relates to a method and apparatus for differentiating between a strain of the PFM and a contraction of the PFM of a female subject/user.

2. Present State of the Art

Personal exercise devices are in general known, see for instance the Tao devices invented by Yanev which are essentially executive toys, and software solutions to control them, allowing busy office workers or travellers to clench the device between their palms or knees. The Yanev patents are numerous, but include WO2013192084A1, WO2011130218A1, WO201278718A1, US20130337976A1, US20130337975A1, US20130337974A1, US20120150074A1, US20110250575A1, U.S. Pat. No. 8,343,013B1 and U.S. Pat. No. 8,172,723B1.

Whilst such devices are focused on working clearly visible muscles such as those in the arms and thighs, providing devices for working and/or monitoring the action of the body's more internal muscles is significantly more challenging. In particular, it is difficult to determine whether or not an exercise of the Pelvic Floor has been performed correctly due to their presence within the body where they cannot easily be visually observed. Consequently, it is very hard for an individual or an instructor or health care professional to actually know whether the PFMs of a subject are being exercised correctly. Not only is it advantageous to have a strong core to prevent back and other postural problems, there are also various conditions associated with damage to the PFMs, for instance through having undergone pregnancy and labour, or simply having weak PFMs (which may cause stress incontinence, sexual problems and prolapse).

Various attempts have been made to provide devices for working and/or monitoring the action of the PFM. For example, US2014/016945 discloses a hinged, spring loaded and purely mechanical device. This looks unattractive for use in such a sensitive area and collects no data. U.S. Pat. No. 8,147,429 teaches the use of a whole "station," based around a table or chair. This is best described as a research tool. U.S. Pat. No. 5,483,832 and EP0583456 teach the use of a pneumatic device with deformable chambers. However, pneumatic devices are not terribly sensitive nor reliable. Similarly, EP1034016 discloses the use of an inflatable system.

As an alternative to these, some approaches focus on making use electromyography (EMG) to record the electrical activity produced by the PFM. For instance, EP2029220 relates to a device comprising electrodes which are positioned at several locations along the length and around the circumference of a vaginal probe, the electrodes detecting EMG signals. The use of electrodes is awkward and so it is hard to ensure correct private use, as well as being unattractive. Furthermore, inter-day reliability is low. U.S. Pat. No. 8,340,786 relates to a device and method for treatment of urinary and faecal incontinence. The device is invasive as it inserts an electrode into the patient's muscle to stimulate it.

As a yet further alternative, WO2013/147992 has a plurality of tactile sensors around its periphery, i.e. on its external face, to directly contact the vaginal wall, allowing it to record the elasticity of the vagina, which is useful in diagnosing certain muscle deformations such as womb prolapse. Similarly, WO2012/079127 relates to an apparatus that makes use of a pressure transducer that relies on pneumatics to provide an indication of the strength of a PFM action. Other disclosures include WO 00/09013 (Medscand Medical AB), WO 2012/031235 (Artann Lab, Inc.) and WO 2012/138232 (Pelvital AS).

One of the issues with the existing devices is that it is very hard to determine whether a female subject has performed a contraction of the PFM or a strain of the PFM. Currently, the only methods available for accurately assessing whether a subject has performed a contraction of the PFM or a strain of the PFM are palpation, visual observation, electromyography, ultrasound, or magnetic resonance imaging. However, methods such as electromyography, ultrasound, and magnetic resonance imaging require specialist equipment and are therefore uneconomical and inconvenient, whilst manual methods such as palpation and visual observation require the presence of a physiotherapist or doctor on every occasion that this distinction is required and can cause embarrassment for the female subject.

SUMMARY OF THE INVENTION

It is therefore desirable to provide a system that can differentiate between a strain of the PFM and a contraction of the PFM of a female subject/user that is both straightforward to use and economical to produce.

Therefore, according to a first aspect there is provided a method of differentiating between a strain of the pelvic floor muscles (PFM) of a subject and a contraction of the PFM of the subject. The method comprises receiving data generated by an orientation sensor provided within a vaginal probe device that is located within the vaginal canal of the subject, the vaginal probe device comprising a housing containing the orientation sensor; utilizing a processor to process data generated by the orientation sensor to determine a direction of rotation of the vaginal probe device during a measurement period. The method further comprises, when the processor determines that the vaginal probe device has rotated in the cranial-ventral direction relative to the subject, generating an output indicating that there has been a contraction of the PFM during the measurement period; and when the processor determines that the vaginal probe device has rotated in the caudal-dorsal direction relative to the subject, generating an output indicating that there has been a strain the PFM during the measurement period. By way of example, the measurement period/phase may be between 200 ms and 2000 ms in length.

The orientation sensor data may be used by the processor to monitor the orientation of the vaginal probe device during the measurement period, and the processor then determines the direction of rotation of the vaginal probe device by monitoring the change in the orientation of the vaginal probe device during the measurement period.

The orientation sensor data may comprise a time series sequence of data points, and the processor may then determine a direction of rotation of the vaginal probe device when the change in the orientation of the vaginal probe device during the measurement period continues in the same direction for a predefined number of contiguous data points.

The method may further comprise, subsequent to locating the vaginal probe device within the vaginal canal of a subject, and prior to the start of the measurement period, initiating an internal calibration period; utilizing the processor to process data generated by the orientation sensor during the internal calibration period to calculate one or more values that are indicative of noise present within the subject; and utilizing the one or more values that are indicative of noise present within the subject to eliminate noise from the orientation sensor data generated during the measurement period.

In some embodiments, the internal calibration phase/period may be optimised for personal use. By way of example, the internal calibration phase/period may be between 200 ms and 2000 ms in length. In some embodiments, the internal calibration phase/period is preferably approximately 500 ms in length, preferably 1000-2500 ms, preferably 1500-2500 ms, preferably 1800-2200 ms or preferably approximately 2000 ms in length.

Alternatively, the internal calibration phase/period may be optimised for use by a physiotherapist, instructor or health care professional. For example, the internal calibration phase/period may be between 200 ms and 7000 ms or even 8000 ms in length. In some embodiments, the internal calibration phase/period is preferably approximately 4000-6000 ms in length, preferably 4500-5500 ms, preferably 5000-6000 ms, preferably 4000-5500 ms or preferably approximately 5000 ms in length. Longer internal calibration phase/period are preferable in terms of accuracy and longer wait times, especially without moving, are typically more acceptable and indeed beneficial in environments controlled by physiotherapists, instructors or health care professionals.

The subject's body noise may change over time, or between days, depending on their level of stress or relaxation, or fatigue. To more accurately eliminate the body noise of the subject for a specific measurement period the internal calibration phase and the measurement period may be implemented contiguously (or continuously) during a sampling period. By way of example, the sampling period/phase may then be between 400 ms and 4000 ms in length.

The method may further comprise, prior to locating the vaginal probe device within the vaginal canal of a subject, initiating an external calibration phase during which the vaginal probe device is held stationary; utilizing the processor to process data generated by the orientation sensor during the external calibration phase to calculate one or more values that are indicative of noise present within the device; and utilizing the one or more values that are indicative of noise present within the device when calculating the one or more values that are indicative of noise present within the subject.

The one or more values that are indicative of noise generated within the subject may comprise any of an upper threshold and a lower threshold for the orientation of the vaginal probe device, and the step of utilizing the one or more values that are indicative of noise present within the subject to eliminate noise from the orientation sensor data generated during the measurement period may then comprise applying any of the upper threshold and the lower threshold to the orientation of the vaginal probe device measured during the measurement period.

The method may further comprise detecting the initiation of a PFM movement/action; and commencing the measurement period at the initiation of the PFM movement. The step of detecting the initiation of a PFM movement may comprise any of receiving a user input indicating the initiation of a PFM movement; utilizing the orientation sensor data to detect significant movement of the vaginal probe device as an indication of the initiation of a PFM movement; and utilizing a force sensor of the vaginal probe device to detect a compressive force acting on the vaginal probe device as an indication of the initiation of a PFM movement.

The orientation sensor may comprise one or more of an accelerometer, a geomagnetic field sensor, a magnetometer, and a gyroscopic sensor. Preferably, the orientation sensor comprises an accelerometer, and accelerometer data generated by the accelerometer is then used by the processor to monitor the orientation of the vaginal probe device relative to gravity.

According to a second aspect of the invention there is provided a system for differentiating between a strain of the PFM of a subject and a contraction of the PFM of the subject. The system comprises a vaginal probe device configured to be located in the vaginal canal of the subject, the vaginal probe device comprising a housing containing an orientation sensor; and a processor. The processor is configured to receive data generated by the orientation sensor; and to process data generated by the orientation sensor to determine a direction of rotation of the vaginal probe device during a measurement period. When the processor determines that the vaginal probe device has rotated in the cranial-ventral direction relative to the subject, the processor is configured to generate an output indicating that there has been a contraction of the PFM during the measurement period; and when the processor determines that the vaginal probe device has rotated in the caudal-dorsal direction relative to the subject, the processor is configured to generate an output indicating that there has been a strain of the PFM during the measurement period.

The system may further comprise a computer device configured to communicate with the vaginal probe device, wherein the computer device comprises an output device configured to convey the output generated by the processor to a user of the computer device. The processor may be provided within the vaginal probe device, and the vaginal probe device may then further comprise a transmitter configured to send the output generated by the processor to the computer device. Alternatively, the processor may be provided within the computer device and the vaginal probe device may then further comprise a transmitter configured to send the data generated by the orientation sensor to the computer device.

The processor may be configured to use the orientation sensor data to monitor the orientation of the vaginal probe device during the measurement period, and to determine the direction of rotation of the vaginal probe device by monitoring changes in the orientation of the vaginal probe device during the measurement period.

The orientation sensor data may comprise a time series sequence of data points, and the processor may then be configured to determine a direction of rotation of the vaginal probe device when the change in the orientation of the vaginal probe device during the measurement period continues in the same direction for a predefined number of contiguous data points.

The processor may be configured to, upon initiation of an internal calibration phase, process data generated by the orientation sensor during the internal calibration phase to calculate one or more values that are indicative of noise present within the subject, and to utilize the one or more values that are indicative of noise present within the subject to eliminate noise from the orientation sensor data generated during the measurement period.

The processor may be configured to, upon initiation of an external calibration phase during which the vaginal probe device is held stationary, process data generated by the orientation sensor during the external calibration phase to calculate one or more values that are indicative of noise present within the device, and to utilize the one or more values that are indicative of noise present within the device when calculating the one or more values that are indicative of noise present within the subject.

The processor may be configured to calculate one or more values that are indicative of noise generated within the subject that comprise any of an upper threshold and a lower threshold for the orientation of the vaginal probe device, and to apply any of the upper threshold and the lower threshold to the orientation of the vaginal probe device measured during the measurement period.

The processor may be configured to detect the initiation of a PFM movement; and commence the measurement period at the initiation of the PFM movement. The processor may be configured to detect the initiation of a PFM movement upon receiving a user input indicating the initiation of a PFM movement. Alternatively, the processor may be configured to utilize the orientation data to detect significant movement of the vaginal probe device as an indication of the initiation of a PFM movement. Alternatively, the vaginal probe device may further comprise a force sensor configured to detect a compressive force acting on the vaginal probe device and to transmit force data to the processor, and the processor may then be configured to utilize the force data to detect compressive force acting on the vaginal probe device as an indication of the initiation of a PFM movement.

The orientation sensor may comprise one or more of an accelerometer, a geomagnetic field sensor, a magnetometer, and a gyroscopic sensor. Preferably, the orientation sensor comprises an accelerometer, and the processor may then be configured to process accelerometer data generated by the accelerometer to monitor the orientation of the vaginal probe device relative to gravity.

According to a third aspect of the present invention there is provided a vaginal probe device for use in differentiating between a strain of the PFM of a subject and a contraction of the PFM of the subject. The vaginal probe device comprises a housing configured to be located within the vaginal canal of the subject; an orientation sensor contained within the housing; and a transmitter configured to send data generated by the vaginal probe device to a computer device located externally relative to the subject.

The transmitter may be configured to send orientation sensor data generated by the orientation sensor to the computer device.

The vaginal probe device may further comprise a processor contained within the housing that is configured to receive data generated by the orientation sensor; to process the orientation sensor data to determine a direction of rotation of the vaginal probe device during a measurement period. When the processor determines that the vaginal probe device has rotated in the cranial-ventral direction relative to the subject, the processor is configured to then generate an output indicating that there has been a contraction of the PFM during the measurement period; and the processor determines that the vaginal probe device has rotated in the caudal-dorsal direction relative to the subject, the processor is configured to then generate an output indicating that there has been a strain of the PFM during the measurement period.

The transmitter may then be configured to send the output generated by the processor to the computer device.

The orientation sensor may comprise one or more of an accelerometer, a geomagnetic field sensor, a magnetometer, and a gyroscopic sensor.

According to a fourth aspect of the present invention there is provided a computer device for use in differentiating between a stain of the PFM of a subject and a contraction of the PFM of the subject. The computer device comprises a receiver configured to receive orientation data from a vaginal probe device; and a processor. The processor is configured to process the orientation data to determine a direction of rotation of the vaginal probe device during a measurement period, when it is determined that the vaginal probe device has rotated in the cranial-ventral direction relative to the subject, the processor is then configured to generate an output indicating that there has been a contraction of the PFM during the measurement period; and when it is determined that the vaginal probe device has rotated in the caudal-dorsal direction relative to the subject, the processor is then configured to generate an output indicating that there has been a strain of the PFM during the measurement period. The computer device further comprises an output device configured to convey the output generated by the processor to a user of the computer device.

According to a fifth aspect of the present invention there is provided a computer readable medium storing computer interpretable instructions which when interpreted by a programmable computer cause the computer to, upon receipt of orientation data from a vaginal probe device located within the vaginal canal of a subject, process the orientation data to determine a direction of rotation of the vaginal probe device during a measurement period; when it is determined that the vaginal probe device has rotated in the cranial-ventral direction relative to the subject, generate an output indicating that there has been a contraction of the PFM during the measurement period; and when it is determined that the vaginal probe device has rotated in the caudal-dorsal direction relative to the subject, generate an output indicating that there has been a strain of the PFM during the measurement period.

BRIEF DESCRIPTION OF THE DRAWINGS

The present invention will now be more particularly described by way of example only with reference to the accompanying drawings, in which.

DETAILED DESCRIPTION OF THE PREFERRED EMBODIMENTS

Overview of System

The present inventors have recognised that, during a contraction of the PFM (referred to as a PFM ascent) the orientation of the vagina changes by moving in the cranial/ventral direction (i.e. in either the cranial direction, ventral direction, or cranial-ventral direction), and that in contrast during a strain of the PFM (referred to as a PFM descent) the orientation of the vagina changes by moving in the caudal/dorsal direction (i.e. in either the caudal direction, dorsal direction, or caudal-dorsal direction).

The present inventors have therefore developed a system and method for differentiating between a strain of the PFM and a contraction of the PFM of a female subject during an attempted voluntary contraction, in which a vaginal probe device is located within the vaginal canal of a subject/an individual. The vaginal probe device is configured to maintain its orientation relative to the longitudinal axis of the vaginal canal such that the movement of the vagina under the action of PFM will cause a corresponding movement of the vaginal probe device. The direction of rotation of the vaginal probe device relative to the subject can therefore be determined, and the determined direction of rotation used to determine whether there has been a contraction of the PFM or a strain of the PFM.

Figure 1:
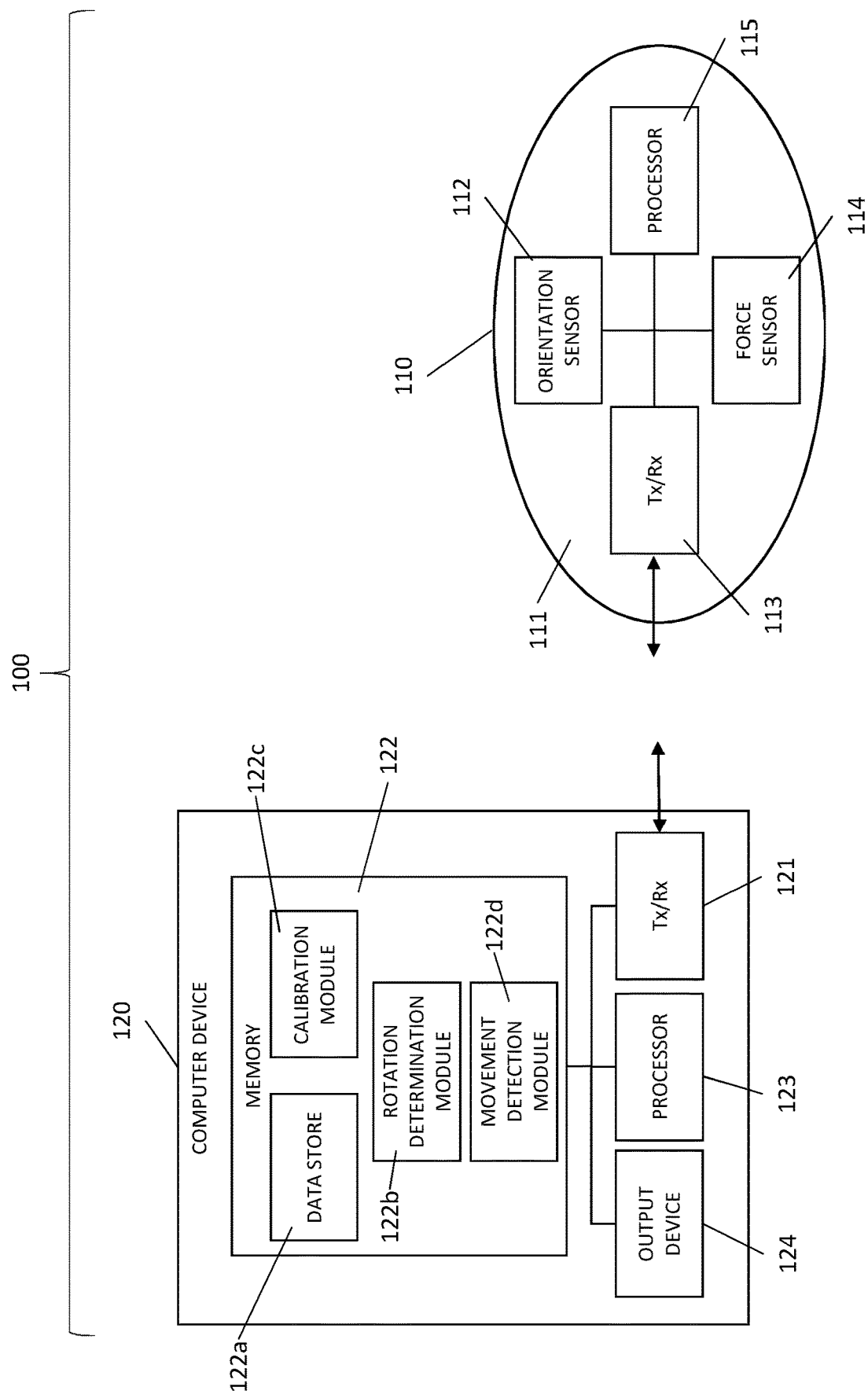
FIG. 1 illustrates schematically an example embodiment of a system suitable for monitoring the action of the PFM as described herein.

FIG. 1 illustrates schematically an example embodiment of a system 100 suitable for monitoring the action of the PFM, and differentiating between a strain of the PFM/PFM descent and a contraction of the PFM/PFM ascent of a female subject. The system 100 comprises a vaginal probe device 110 configured to be located in the vaginal canal of a subject/an individual and configured to maintain its orientation relative to the longitudinal axis of the vaginal canal, and a computer device 120 configured to communicate with the vaginal probe device 110.

Preferably, the vaginal probe device 110 and the computer device 120 are configured to communicate with each other wirelessly, e.g. using Bluetooth™, Wi-Fi™, ZigBee™, NFC, 3G, 4G etc., although the vaginal probe device 110 and the computer device 120 could also be configured to communicate via a wired communication interface.

The vaginal probe device 110 comprises a housing 111 containing an orientation sensor 112 configured to monitor the orientation of the vaginal probe device 110, and a transceiver 113 configured to transmit data to and receive data from the computer device 120. By way of example, the orientation sensor 112 could comprise one or more of an accelerometer (e.g. a two axis or three axis accelerometer), a geomagnetic field sensor/magnetometer, and a gyroscopic sensor.

The housing 111 of the vaginal probe device 110 is configured allow the vaginal probe device 110 to be easily located in the vaginal canal of a subject/an individual and to ensure that the vaginal probe device 110 maintains its orientation relative to the longitudinal axis of the vaginal canal.

The vaginal probe device 110 can optionally further comprise a force sensor 114 configured to monitor any compressive force acting on the vaginal probe device 110. In addition, the vaginal probe device 110 can optionally further comprise a processor 115 that can be configured to process data generated by the orientation sensor 112 and/or the force sensor 114 if so required.

The computer device 120 can be implemented as a combination of computer hardware and software, and comprises a transceiver 121, a memory 122, a processor 123, and an output device unit 124. The transceiver 121 is configured to transmit data to and receive data from the vaginal probe device 110, and the output device unit 124 is configured to convey output data provided by the processor 123 to a user of the computer device 120. By way of example, the output device unit 124 could comprise any of a user interface/display device, a haptic feedback device, or an audio output device such as a speaker.

The memory 122 typically stores the various programs/executable files that are implemented by the processor 123, including any system configuration data and any other data that may be of use to the computer device 120. In particular, the data stored by the memory 122 can include but is not limited to a data store 122a that is configured to store data provided to, obtained by, or generated by the computer device 120.

In this embodiment, the processor 123 is configured to implement the processing necessary to monitor the action of the PFM of a female subject that is using the vaginal probe device 110, and to differentiate between a strain of the PFM/PFM descent and a contraction of the PFM/PFM ascent. As such, the processor 123 is configured to implement any of the functionality required in order to execute any of the processes, perform any of the actions, and maintain any items of data described herein. In particular, the processor 123 is configured to operate in accordance with programming instructions input for example as data stored in a data storage medium such as a disc and/or as a signal input into the computer device 120 for example from a remote database by transmission over a communications network (not shown) such as the Internet and stored in the memory 122.

As will be described in more detail below, the programming instructions comprise instructions to cause the computer device 120 to become configured to process orientation data generated by the orientation sensor 112 to generate an output that indicates either that there has been a contraction of the PFM or a strain of the PFM during a measurement period/phase.

When programmed by the programming instructions, the computer device 120 effectively becomes configured into a number of functional units for performing processing operations. Examples of such functional units are shown in FIG. 1. The units illustrated in FIG. 1, are however, notional and are shown for illustration purposes only to assist understanding; they do not necessarily represent exact units and connections into which the processor, memory etc. of the computer device 120 become configured.

Referring to the functional units shown in FIG. 1, a data store 122a is provided for storing orientation data obtained/received from the vaginal probe device 120. A rotation determination module 122b is also provided that is configured to process the orientation data to determine a direction of rotation of the vaginal probe device 120 during a measurement period/phase and to generate an output indicating that there has been either a contraction or a strain of the PFM. By way of example, the orientation data provided by the orientation sensor 112 will typically comprise a time series sequence of data points, with each data point defining the measured orientation of the vaginal probe device at a particular point in time. The rotation determination module 122b could then be configured to determine a direction of rotation of the vaginal probe device when the change in the orientation of the vaginal probe device during the measurement period/phase continues in the same direction for a predefined number of contiguous data points.

In addition, a calibration module 122c is provided that is configured to process the orientation data to generate parameters for calibrating the processing implemented by the system 100. In particular, in order to calibrate the orientation data for any noise that is present within the subject, the vaginal probe device 110 would be located within the vaginal canal of the subject, and an internal calibration phase/period initiated. Upon initiation of the internal calibration phase/period for the vaginal probe device 110, the calibration module 122c would be then configured to process data generated by the orientation sensor 112 during the internal calibration phase/period to calculate one or more values that are indicative of noise present within the subject. These values that are indicative of noise present within the subject can then used by the rotation determination module 122b to eliminate noise from the orientation data generated during the measurement period/phase.

By way of example, the values that are indicative of noise generated within the subject could comprise any of an upper threshold and a lower threshold for changes in the orientation of the vaginal probe device 112. The rotation determination module 122b would then be configured to apply any of the upper threshold and the lower threshold to the orientation sensor data generated during the measurement period/phase.

Furthermore, it may also be desirable to calibrate the system 100 to take into account noise that is present within the vaginal probe device 110 itself. To do so, whilst outside of a subject the vaginal probe device 110 could be held stationary, and an external calibration phase/period initiated. Upon initiation of an external calibration phase/period, the calibration module 122c would be then configured to process data generated by the orientation sensor 122 during the external calibration phase/period to calculate one or more values that are indicative of noise present within the device. These values that are indicative of noise present within the device 110 would then be used by the calibration module 122c when calculating the one or more values that are indicative of noise present within the subject (i.e. when performing an internal calibration).

Optionally, a movement detection module 122d can also be provided that is configured to detect the initiation of a PFM movement, and commence a measurement period/phase at the initiation of the PFM movement. The movement detection module 122d can be configured to detect the initiation of a PFM movement upon receiving a user input indicating the initiation of a PFM movement. Alternatively, the movement detection module 122d can be configured to detect the initiation of a PFM movement by utilizing the orientation data to detect significant movement of the vaginal probe device 110 as an indication of the initiation of a PFM movement. As a further alternative, the movement detection module 122d can be configured to detect the initiation of a PFM movement by processing force data generated by the optional force sensor 114 to detect a significant compressive force acting on the vaginal probe device 110 as an indication of the initiation of a PFM movement.

Figure 2:
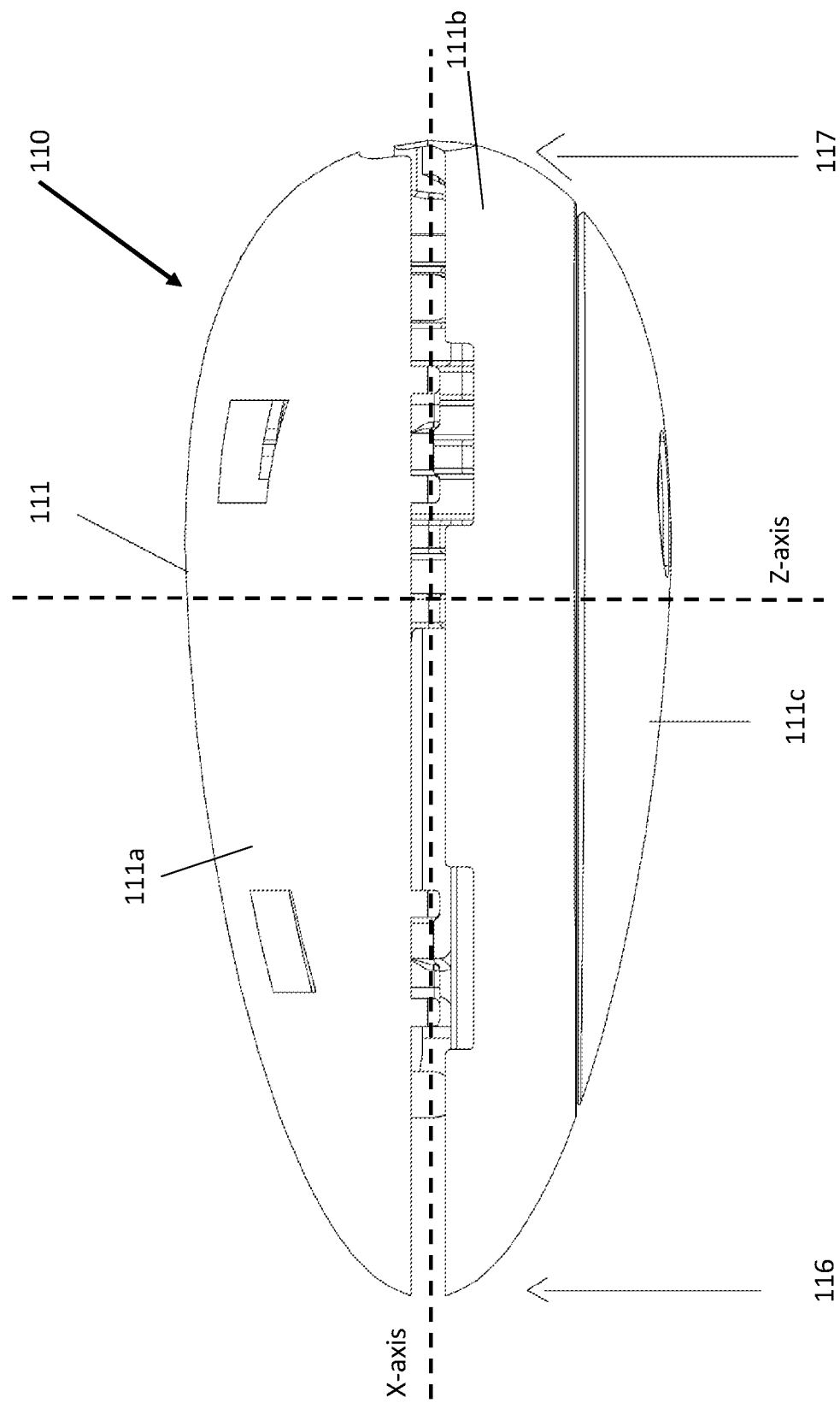
FIG. 2 illustrates a side view of an exemplary embodiment of a vaginal probe device of the system of FIG. 1.
Figure 3:
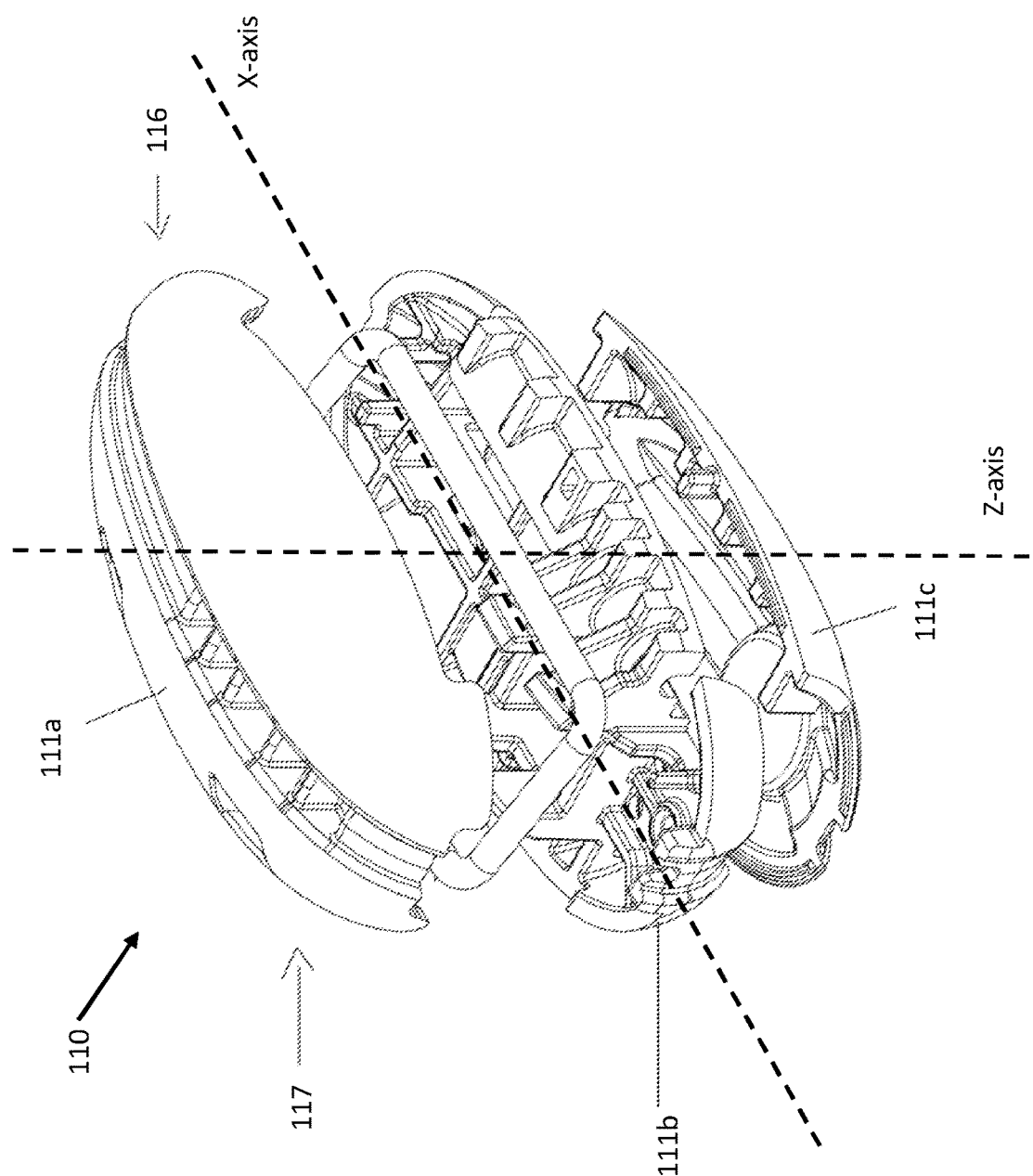
FIG. 3 shows a partially exploded perspective view of the vaginal probe device of FIG. 2.

By way of example, FIGS. 2 and 3 illustrate an exemplary embodiment of a suitable vaginal probe device 110. As shown in FIGS. 2 and 3, the housing 111 of this exemplary vaginal probe device 110 is substantially ovate or ovoid-shaped, has a nose 116 and a tail 117, and comprises three parts: an upper 111a, middle 111b, and lower 111c each of which can be made, for instance by injection moulding, from a moulded hard plastic. However, the housing 11 could equally be substantially ellipsoid in shape. The ovoid or ellipsoid shape of the vaginal probe device 110 is advantageous as it both aids in insertion of the vaginal probe device 110 and helps to stabilise the device in use, for instance by preventing the device from rotating away from/out of alignment with the longitudinal axis of the vagina (i.e. preventing pitch or yaw of the vaginal probe device 110 relative to the longitudinal axis of the vagina).

Figure 4:
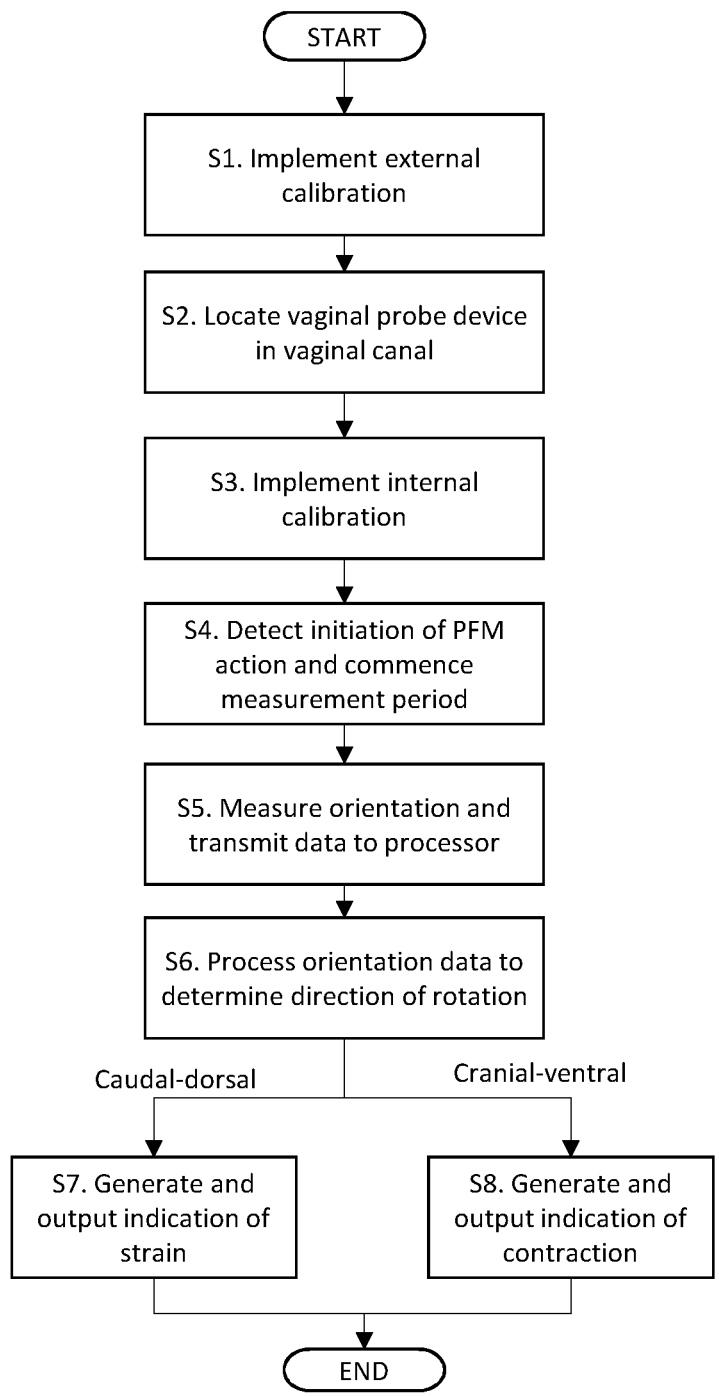
FIG. 4 is a flow diagram illustrating an embodiment of a process for monitoring the action of the PFM in accordance with the methods described herein.

The housing 111 should be suitably sized to fit within the vagina of a female subject and to maintain its orientation relative to the longitudinal axis of the vaginal canal. Some elements, such as wires, may protrude from the vaginal probe device 110 provided that the bulk of the housing 111 is positioned within the vagina Use of System in Monitoring the Pelvic Floor Muscles FIG. 4 is a flow diagram illustrating an embodiment of a process for monitoring the action of the PFM, and differentiating between a strain of the PFM and a contraction of the PFM of a female subject. The steps performed are as follows:

S1. Prior to locating the vaginal probe device 110 within the vaginal canal of a subject, an external calibration is implemented in order to calculate one or more values that are indicative of noise present within the vaginal probe device 110 itself.

In this regard, the orientation sensor 112 may have an inherent degree of error, or noise. Therefore, during an external calibration phase/period, and whilst the vaginal probe device 110 is outside of the subject and is held stationary, the orientation data generated by the orientation sensor 112 is measured to determine if there is any noise. If there are no fluctuations in the data generated by orientation sensor 112, then it can be concluded that there is no device noise. However, any fluctuation in the data generated by orientation sensor 112 can be averaged to determine one or more values for the device noise. The calculated device noise values can then be stored in the memory 122 of the computer device 120.

S2. The vaginal probe device 110 can then be located within the vaginal canal of a subject/an individual.

S3. Once the vaginal probe device 110 has been located within the vaginal canal of a subject, an internal calibration is implemented in order to calculate one or more values that are indicative of noise present within the subject.

In this regard, once the vaginal probe device 110 is in situ within the subject it will be moving, even when the subject is not intentionally moving. This movement can be referred to as 'body noise' generated by involuntary slight muscular movements and needs to be accounted for when determining any change in orientation of the vaginal probe device 110. Therefore, during an internal calibration phase/period, with the vaginal probe device 110 located in the vaginal canal of the subject and whilst the subject is not voluntarily attempting to contract their PFM, the orientation data generated by the orientation sensor 112 is measured to determine if there is any noise. Any fluctuation in the data generated by orientation sensor 112 can then be used to determine one or more values for the body noise of the subject.

By way of example, the one or more values that are indicative of noise generated within the subject preferably comprise an upper threshold and a lower threshold that are to be applied to orientation data to eliminate noise.

These thresholds could be determined by calculating both the mean of the orientation measurements taken during the internal calibration phase/period and the range of the orientation measurements taken during the internal calibration phase/period, and then calculating:

Upper threshold=mean orientation+(orientation range/2)+device noise

Lower threshold=mean orientation−(orientation range/2)−device noise wherein the device noise is the noise value determined during the external calibration phase (step S1). These thresholds can then be applied to the orientation data detected during a subsequent measurement period to provide a level of confidence that changes in the orientation of the vaginal probe device 110 relate to voluntary movements of the PFM.

S4. After the internal calibration has been completed, the initiation of a significant PFM movement/action can then be detected, and the detection of significant PFM movement/action used to initiate the commencement a measurement period/phase. The initiation of a significant PFM movement can be detected upon receiving a user input indicating the initiation of a PFM movement. Alternatively, the initiation of a significant PFM movement can be detected by utilizing the orientation data to detect significant movement of the vaginal probe device 110. As a further alternative, the initiation of a significant PFM movement can be detected by utilising force data generated by the optional force sensor 114 to detect a significant compressive force acting on the vaginal probe device 110.

S5. During the measurement period/phase the orientation sensor 112 is used to monitor the orientation of the vaginal probe device 110, and the orientation data transmitted for use by the processor 123.

S6. Upon receiving the orientation data generated by the orientation sensor 112 during the measurement period/phase, the processor 123 processes the orientation data to determine the direction of rotation of the vaginal probe device 110.

In this regard, the orientation sensor data would typically comprise a time series sequence of data points, with each data point defining the measured orientation of the vaginal probe device 110 at a particular point in time. The processor would then be configured to determine a direction of rotation of the vaginal probe device 110 when the change in the orientation of the vaginal probe device 110 during the measurement period/phase continues in the same direction for a predefined number of contiguous data points.

S7. If the processor 123 determines that the vaginal probe device 110 has rotated in the cranial-ventral direction relative to the subject, the processor 123 then generates an output indicating that there has been a contraction of the PFM during the measurement period/phase, and outputs this indication to the output device 124 of the computer device 120 so that the output can be conveyed to a user.

S8. If the processor 123 determines that the vaginal probe device has rotated in the caudal-dorsal direction relative to the subject, the processor 123 then generates an output indicating that there has been a strain of the PFM during the measurement period/phase, and outputs this indication to the output device 124 of the computer device 120 so that the output can be conveyed to a user.

Figure 5:
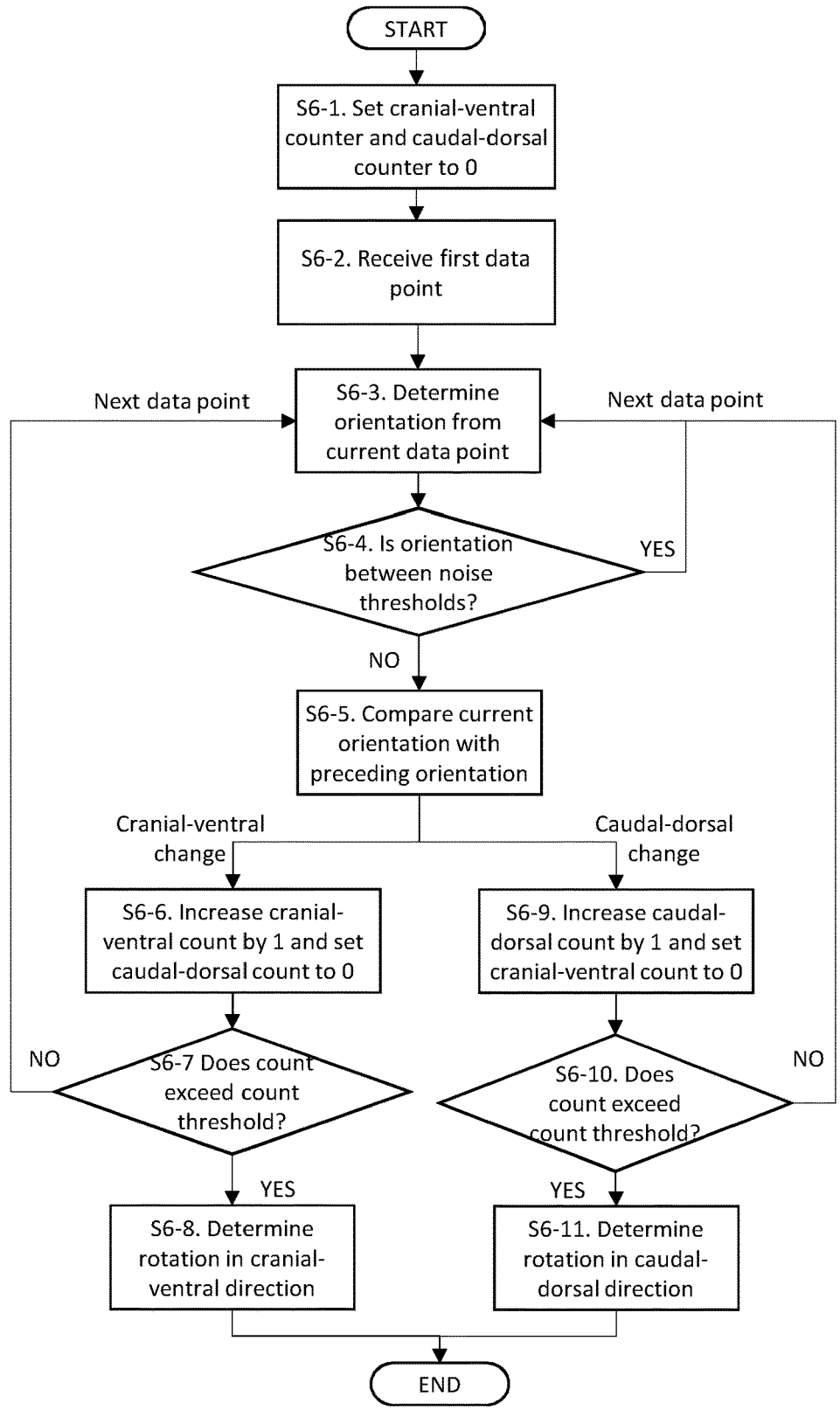
FIG. 5 is a flow diagram illustrating an embodiment of a process for processing orientation data to determine the direction of rotation of a vaginal probe device in accordance with the methods described herein.

FIG. 5 is a flow diagram illustrating an embodiment of a process of step S6 described above, for processing the orientation data to determine the direction of rotation of the vaginal probe device. The steps performed are as follows:

S6-1. To initialise the processing, both a cranial-ventral counter and a caudal-dorsal counter that are stored in the memory 122 are set/reset to 0. The cranial-ventral counter and the caudal-dorsal counter are used to maintain a count of the number of contiguous data points that have indicated rotation in the cranial-ventral and caudal-dorsal directions respectively.

S6-2. The processor 123 then begins to receive orientation data from the orientation sensor 112, receiving a first data point from orientation sensor 112, wherein the data point defines the data generated by the orientation sensor 112 of the vaginal probe device 110 at a particular point in time.

S6-3. The processor 120 then processes the current data point to determine the orientation of the vaginal probe device 110 relative to the subject.

By way of example, if the orientation sensor 112 is an accelerometer, then a data point generated by the orientation sensor could comprise two-axis (x and z axis) acceleration data, wherein the two-axes of the accelerometer are defined relative to the vaginal probe device 110 as illustrated in the examples of FIGS. 2 and 3. In this case, the orientation of the vaginal probe device relative to gravity can therefore be determined by appropriate processing of the two-axis acceleration data. For example, the orientation of the vaginal probe device could then be determined by processing that implements the pseudo code given below, in which 0 degrees is defined as being in the dorsal/posterior direction relative to the subject, 90 degrees is in the cranial direction relative to the subject, 180 degrees is in the ventral direction relative to the subject, and 270 degrees is in the caudal direction relative to the subject, and the subject is assumed to be standing (i.e. such that gravity acts in caudal direction at 270 degrees):

```
Method CalculateOrientation(DataPoint) {
    x = DataPoint.x
    z = DataPoint.z
    if (z == 0 and x < 0) {
        then orientation = 90
    } else if (z == 0 and x > 0) {
        then orientation = 270
    } else if (x == 0 and z > 0) {
        then orientation = 180
    } else {
        orientation = (atan(x/z)*180)/pi
        if (z > 0 and x != 0) {
            then orientation = orientation + 180
        } else if (x > 0 and z < 0) {
            then orientation = orientation + 360
        }
    }
    return orientation
}
```

S6-4. The processor then determines if the determined orientation of the vaginal probe device is between the upper and lower thresholds generated during the calibration phases as a means for eliminating noise from the orientation data. If the determined orientation is between the upper and lower noise thresholds, then the processor stops processing the current data point, sets/resets the cranial-ventral counter and the caudal-dorsal counter to 0, and returns to step S6-3 and begins processing the next data point.

S6-5. If the orientation determined from the current data point is not between the upper and lower noise thresholds (i.e. the orientation determined from the current data point exceeds one or other of the upper and lower thresholds), then the processor compares the orientation determined from the current data point with the orientation determined from the preceding data point. In this regard, as the vaginal probe device is configured to maintain its orientation relative to the longitudinal axis of the vaginal canal, the x-axis of the vaginal probe device (i.e. the longitudinal axis of the vaginal probe device) will be substantially aligned with longitudinal axis of the vaginal canal. The change in the orientation of the vaginal probe device between data points can therefore be used to determine the direction of rotation of the vaginal probe device relative to the subject.

S6-6. If the comparison of the orientation determined from the current data point with the orientation determined from the preceding data point indicates that the change in orientation of the vaginal probe device has been in the cranial-ventral direction, then the cranial-ventral counter is increased by 1 and the caudal-dorsal counter is set/reset to 0. In this regard, expanding upon the example given above, the comparison would indicate that the change in orientation of the vaginal probe device has been in the cranial-ventral direction if the orientation determined from the current data point is greater than the orientation determined from the preceding data point (i.e. indicates an increase in the orientation angle).

S6-7. After the cranial-ventral counter has been increased by 1, the processor then determines if the value of the cranial-ventral counter exceeds a minimum count threshold that defines the minimum number of contiguous data points that is required to confirm a direction of rotation. If the value of the cranial-ventral counter does not exceed the minimum count threshold, then the processor returns to step S6-3 and begins processing the next data point.

S6-8 If the value of the cranial-ventral counter does exceed the minimum count threshold, then the processor determines that the rotation of the vaginal probe device is in the cranial-ventral direction, and the processing of the orientation data is complete.

S6-9. From step S6-5, if the comparison of the orientation determined from the current data point with the orientation determined from the preceding data point indicates that the change in orientation of the vaginal probe device has been in the caudal-dorsal direction, then the caudal-dorsal counter is increased by 1 and the cranial-ventral counter is set/reset to 0.

In this regard, expanding upon the example given above, the comparison would indicate that the change in orientation of the vaginal probe device has been in the caudal-dorsal direction if the orientation determined from the current data point is less than the orientation determined from the preceding data point (i.e. indicates a decrease in the orientation angle).

S6-10. After the caudal-dorsal counter has been increased by 1, the processor then determines if the caudal-dorsal counter exceeds the minimum count threshold that defines the minimum number of contiguous data points that is required to confirm a direction of rotation. If the value of the caudal-dorsal counter does not exceed the minimum count threshold, then the processor returns to step S6-3 and begins processing the next data point.

S6-11. If the caudal-dorsal counter does exceed the minimum count threshold, then the processor determines that the rotation of the vaginal probe device is in the caudal-dorsal direction, and the processing of the orientation data is complete.

It will be appreciated that individual items described above may be used on their own or in combination with other items shown in the drawings or described in the description and that items mentioned in the same passage as each other or the same drawing as each other need not be used in combination with each other. In addition, the expression "means" may be replaced by actuator, system, unit or device as may be desirable. In addition, any reference to "comprising" or "consisting" is not intended to be limiting in any way whatsoever and the reader should interpret the description and claims accordingly.

Furthermore, although the invention has been described in terms of preferred embodiments as set forth above, it should be understood that these embodiments are illustrative only. Those skilled in the art will be able to make modifications and alternatives in view of the disclosure which are contemplated as falling within the scope of the appended claims.

By way of example, in the above described embodiments the memory and the processor are provided in the computer device such that it is the computer device that implements the processing necessary to differentiate between a strain of the PFM of a subject and a contraction of the PFM of the subject; however, it is equally possible a memory and a processor could be provided in the vaginal probe device itself, with the processing necessary to differentiate between a strain of the PFM of a subject and a contraction of the PFM of the subject being implemented by the vaginal probe device. In this case, the vaginal probe device would then communicate the output of this processing to the separate computer device so that this output can then be conveyed to a user of the computer device by the output device of the computer device.

As a further example, whilst the internal calibration phase/period and the measurement period/phase have been described in the above embodiments as being implemented separately, it also possible that the internal calibration phase/period and the measurement period/phase could be implemented contiguously during a sampling period/phase. In this case, after location of the vaginal probe device within the vaginal canal of the subject, the vaginal probe device could continually be monitoring the orientation of the device, such that any of the orientation data gathered during this period could be used to implement the internal calibration for body noise. The measurement period/phase would then begin when the initiation of a PFM movement is detected, as described above. The internal calibration phase/period and the measurement period/phase would then be implemented contiguously during a sampling period/phase that takes place after location of the vaginal probe device within the vaginal canal of the subject.

Although the embodiments of the invention described with reference to the drawings comprise computer apparatus and processes performed in computer apparatus, the invention also extends to computer programs, particularly computer programs on or in a carrier, adapted for putting the invention into practice. The program may be in the form of source or object code or in any other form suitable for use in the implementation of the processes according to the invention. The carrier can be any entity or device capable of carrying the program.

For example, the carrier may comprise a storage medium, such as a ROM, for example a CD ROM or a semiconductor ROM, or a magnetic recording medium, for example a floppy disc or hard disk. Further, the carrier may be a transmissible carrier such as an electrical or optical signal which may be conveyed via electrical or optical cable or by radio or other means. When a program is embodied in a signal which may be conveyed directly by a cable or other device or means, the carrier may be constituted by such cable or other device or means. Alternatively, the carrier may be an integrated circuit in which the program is embedded, the integrated circuit being adapted for performing, or for use in the performance of, the relevant processes.

The invention claimed is:

1. A system for differentiating between a pelvic floor muscles (PFM) ascent/contraction and a PFM descent/strain of a subject, the system comprising:
    a vaginal probe device comprising a housing and an orientation sensor within the housing, wherein the housing is configured to be located within the vaginal canal of the subject, wherein the orientation sensor is configured to provide a time sequence of data points, with each data point relating to a single measured value representing the orientation of the entire probe device at a particular point in time; and
    a processor communicating with the probe device and configured to:
        automatically determine a direction of rotation of the entire probe device by monitoring a change in the single measured value representing the orientation of the entire probe device;
        use the determined direction of rotation to automatically determine that the PFM ascent/contraction or the PFM descent/strain has occurred; and
        automatically generate an output indicating the PFM ascent/contraction or the PFM descent/strain.

2. The system of claim 1, wherein the probe device further comprises a force sensor configured to detect a compressive force.

3. The system of claim 2, wherein the processor is further configured to detect an initiation of a PFM movement by detecting a significant compressive force.

4. The system of claim 1, wherein the processor is further configured to determine if the rotation continues in the same direction for a predefined number of contiguous data points.

5. The system of claim 1, wherein the processor is further configured to generate an output if the rotation continues in the same direction for a predefined number of contiguous data points.

6. The system of claim 1, wherein the orientation sensor comprises a single accelerometer.

7. The system of claim 1, wherein the housing comprises a molded hard plastic.

8. The system of claim 1, wherein the housing is substantially ovoid or ellipsoid in shape.

9. The system of claim 1, wherein the housing is shaped to prevent the device from rotating out of alignment with a longitudinal axis of the vaginal canal.

10. The system of claim 1, further comprising:
    a calibration module configured to generate parameters for calibrating the system in order to eliminate noise from orientation data generated during measurement.

11. The system of claim 10, wherein the calibration module, during a calibration phase in which the probe device is located within the vaginal canal while the subject is not voluntary attempting to move PFM, is configured to determine the noise present within the subject.

12. The system of claim 10, wherein the orientation data comprises an upper threshold and a lower threshold to eliminate noise.

13. The system of claim 1, wherein the processor is provided within a computer device located externally relative to the subject, and
    wherein the probe device further comprises a transmitter configured to transmit sensor data to the processor.

14. The system of claim 13, wherein the probe device and the computer device communicate with each other wirelessly, using at least one of Bluetooth, Wi-Fi, Zigbee, NFC, 3G, and 4G.

15. The system of claim 13, wherein the computer device comprises a user interface configured to display output data provided by the processor.

16. A method for differentiating between a pelvic floor muscles (PFM) ascent/contraction and a PFM descent/strain of a subject, the method comprising:
    inserting a vaginal probe device within the vaginal canal of the subject, the probe device comprising a housing and an orientation sensor within the housing, wherein the housing is configured to be located within the vaginal canal of the subject;
    receiving a time sequence of data points data generated by the orientation sensor;
    processing the time sequence of data points to determine for each data point a single measured value representing the orientation of the entire probe device inside the vaginal canal at a particular point in time;
    automatically determining the direction of rotation of the probe device by monitoring a change in the single value of the orientation representing the entire probe device;
    using the determined direction of rotation, automatically determining that the PFM ascent/contraction or the PFM descent/strain has occurred; and
    automatically generating an output indicating the PFM ascent/contraction or the PFM descent/strain.

17. The system of claim 1, wherein the probe device further comprises a second processor configured to process data generated by the orientation sensor.

18. The system of claim 1, wherein the probe device is configured to maintain its orientation relative to the longitudinal axis of the vaginal canal such that a movement of the vagina causes a corresponding movement of the probe device.

19. The system of claim 13, wherein the computer device is configured to detect an initiation of a PFM movement.

20. The system of claim 1, wherein the processor is configured to generate an output through at least one of a user interface/display device, a haptic feedback device, and an audio output device.

* * * * *